United States Patent
Brinz et al.

(10) Patent No.: US 8,758,585 B2
(45) Date of Patent: Jun. 24, 2014

(54) SENSOR FOR DETERMINING GASES AND METHOD FOR MANUFACTURING THE SENSOR

(75) Inventors: Thomas Brinz, Bissingen A.D. Teck (DE); Jane Lewis, Stuttgart (DE); Claus Heppel, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1041 days.

(21) Appl. No.: 12/418,150

(22) Filed: Apr. 3, 2009

(65) Prior Publication Data

US 2009/0205958 A1  Aug. 20, 2009

Related U.S. Application Data

(63) Continuation of application No. 11/000,387, filed on Nov. 30, 2004, now abandoned.

(30) Foreign Application Priority Data

Dec. 5, 2003  (DE) .................................. 103 56 935

(51) Int. Cl.
  *G01N 27/407* (2006.01)
(52) U.S. Cl.
  USPC ....................................... 204/431; 422/82.02
(58) Field of Classification Search
  USPC ............ 204/430, 431, 433; 422/82.01, 82.02;
  205/785.5
  See application file for complete search history.

(56) References Cited

U.S. PATENT DOCUMENTS

| | | | |
|---|---|---|---|
| 4,272,328 A | 6/1981 | Kim et al. | |
| 4,900,405 A | 2/1990 | Otagawa et al. | |
| 4,952,300 A * | 8/1990 | Diamond | 204/406 |
| 5,252,292 A | 10/1993 | Hirata et al. | |
| 5,322,602 A * | 6/1994 | Razaq | 205/788 |
| 5,376,255 A * | 12/1994 | Gumbrecht et al. | 204/426 |
| 5,573,648 A * | 11/1996 | Shen et al. | 204/412 |
| 5,716,506 A * | 2/1998 | Maclay et al. | 204/424 |
| 5,720,862 A | 2/1998 | Hamamoto et al. | |
| 5,841,021 A * | 11/1998 | De Castro et al. | 73/23.2 |
| 5,958,791 A | 9/1999 | Roberts et al. | |
| 6,241,873 B1 | 6/2001 | Namba et al. | |
| 6,682,638 B1 * | 1/2004 | Prohaska et al. | 204/426 |
| 2004/0026267 A1 | 2/2004 | Brinz et al. | |

FOREIGN PATENT DOCUMENTS

EP   1340975   9/2003

OTHER PUBLICATIONS

Encyclopedia Britannica electronic entry for "platinum group"; retrieved from the web on Oct. 23, 2013.*

* cited by examiner

*Primary Examiner* — J. Christopher Ball
(74) *Attorney, Agent, or Firm* — Kenyon & Kenyon LLP

(57) ABSTRACT

A sensor for determining the concentration of a gas in gas mixtures, which has a measuring and a reference electrode as well as a polymer layer, which is in contact with the gas mixture and with the measuring electrode. A pH sensitive electrode is provided as the measuring electrode.

1 Claim, 2 Drawing Sheets

Fig. 1
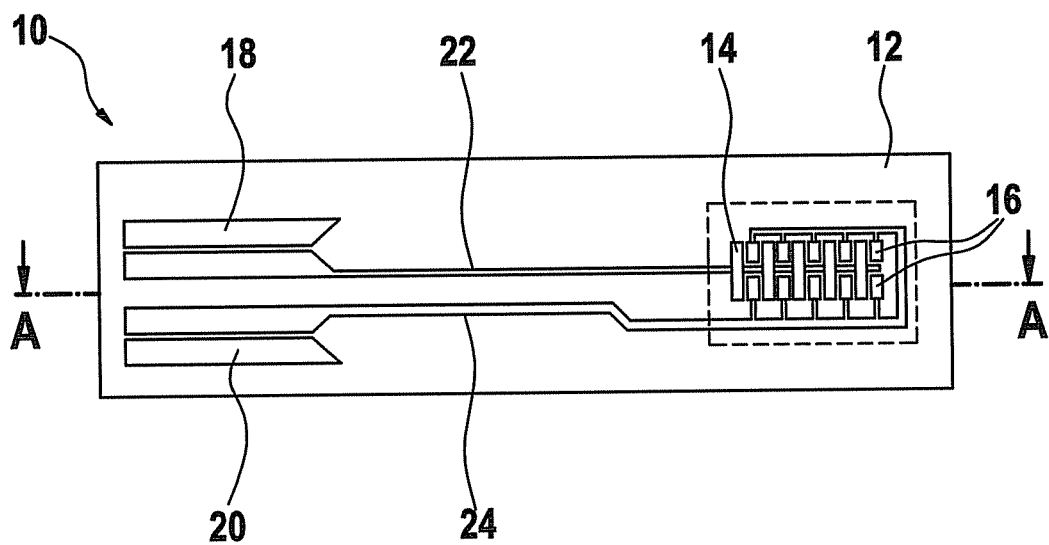
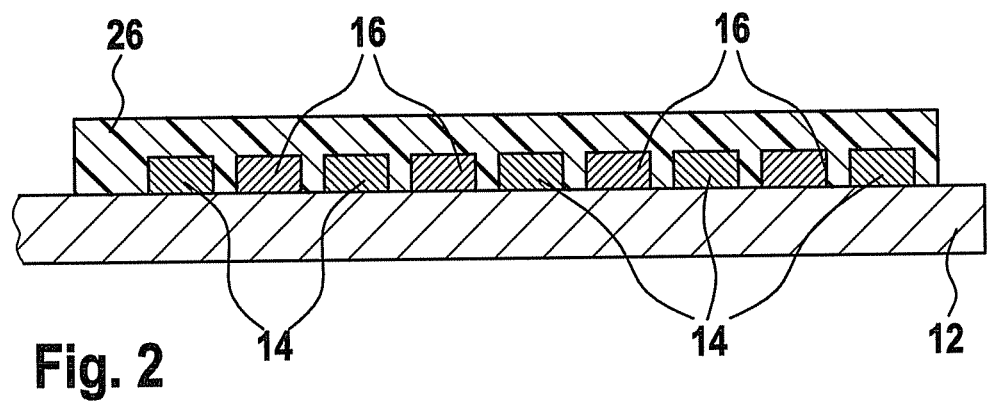
Fig. 2

SENSOR FOR DETERMINING GASES AND METHOD FOR MANUFACTURING THE SENSOR

CROSS-REFERENCE TO RELATED APPLICATION

This application is a continuation of U.S. patent application Ser. No. 11/000,387, which was filed on Nov. 30, 2004, now abandoned, which claimed priority to German Patent Application No DE 103 56 935.9 filed Dec. 5, 2003, all of which are incorporated herein by reference in their entirety.

BACKGROUND INFORMATION

Optical sensors for determining the carbon dioxide content of the air are used, among other things, in fire detectors. Their function is based on the fact that a layer sensitive to carbon dioxide changes color reversibly upon contact with the gas to be determined. This change of color is monitored by a detector, and when a predetermined minimum concentration is exceeded, an alarm is triggered. This measuring method is relatively susceptible to contamination.

Optical $CO_2$ gas sensors normally are made up of a polymeric matrix, e.g. ethylcellulose, a softener and solutizer, e.g. Brij 30, and a basic gas acceptor, e.g. tetraoctylammonium hydroxide. The sensor signal reveals a dependency on the moisture content of the surroundings.

U.S. Pat. No. 6,241,873 describes a carbon dioxide sensor which detects the carbon dioxide content of a surrounding atmosphere in a potentiometric manner. It features a measuring electrode and a reference electrode, which are applied on a substrate. The measuring electrode takes the form of a silver/silver carbonate electrode. The potential of this electrode is a direct function of the carbon dioxide concentration of the surroundings. A disadvantage of this measuring method is the fact that carbonate-containing electrodes are affected by weather influences and thus have only a low stability. Furthermore, the sensor is limited to measuring carbon dioxide.

The present invention is based on the objective of providing a gas sensor for determining different gases in a potentiometric and/or optical manner, which has a high stability and at the same time a high sensitivity.

A further objective lies in the compensation of the moisture-dependency of the sensor.

SUMMARY OF THE INVENTION

The sensor according to the present invention has the advantage that its electrodes are stable over the long term and that its measuring electrode has a high sensitivity with respect to the gas to be determined. This is achieved in that a pH-sensitive electrode is used that detects the pH value of a surrounding polymer. Such pH electrodes have a sufficiently long service life and allow for the determination of various acidic and basic gases.

Thus, for example, the sensor can be designed in such a way that, in addition to measuring the pH value, the optical absorption and the conductivity can be measured as well.

An iridium oxide electrode is particularly suited as a measuring electrode since it is especially robust with respect to environmental influences and does not have to be provided in a pre-expanded state as do comparable glass electrodes.

In a particularly advantageous embodiment, the sensor includes a polymer that has a base or an acid since this results in a quick and effective absorption of the acidic or basic gas to be determined. This further raises the sensitivity and lowers the response time of the sensor.

BRIEF DESCRIPTION OF THE DRAWINGS

FIG. 1 shows a schematic representation of an exemplary embodiment of the sensor according to the present invention in top view.

FIG. 2 shows a sectional view through the sensor represented in FIG. 1 along the sectional line A-A.

DETAILED DESCRIPTION

Figure 3:
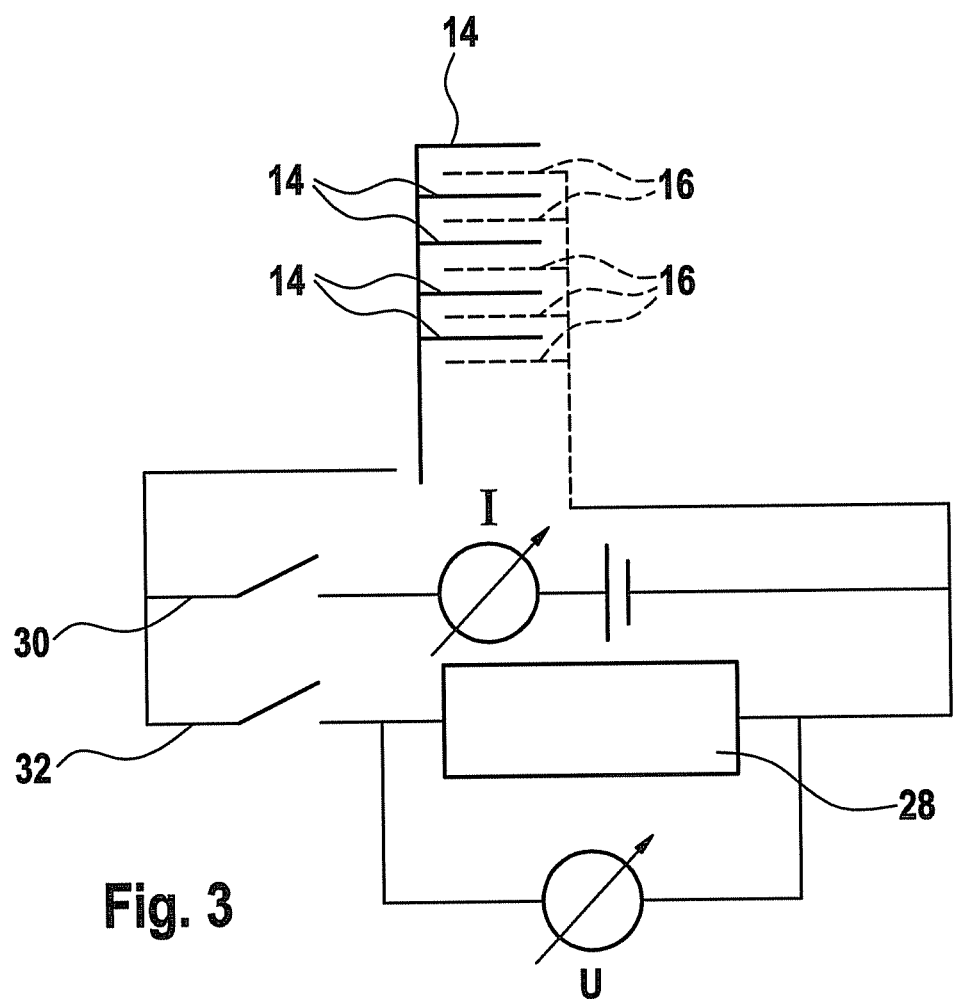
FIG. 3 shows a schematic representation of another exemplary embodiment of the sensor according to the present invention.

Sensor 10 represented in FIGS. 1 and 2 includes a substrate 12 preferably made of a ceramic material such as aluminum oxide for example. On top of this, a measuring electrode 14, preferably in the form of a so-called interdigital electrode, is provided. This forms a comb-like structure. Furthermore, a reference electrode 16 is situated on the substrate which preferably also takes the form of an interdigital electrode, the extensions of comb-like reference electrode 16 engaging with the extensions of the comb-like measuring electrode 14. This ensures a small distance between the measuring electrode 14 and the reference electrode 16 and thus a low impedance of the sensor and at the same time a large electrode surface. A conventional silver/silver chloride electrode is used as a reference electrode, although other electrodes of constant potential such as calomel, antimony or silver/silver bromide electrodes are suitable as well. Electrodes 14, 16 are connected to contact surfaces 18, 20 via circuit traces 22, 24, which are preferably formed by a precious metal-containing hardenable resin such as for example a silver-containing epoxy resin.

Electrodes 14, 16 are preferably coated completely by a gas-sensitive and gas-permeable polymer layer 26, which functions as an electrolyte and which is represented in FIG. 1 as a dashed region. Polymer layer 26 forms a matrix in which there are the compounds responsible for the sensitivity of the sensor. In a preferred embodiment, polymer layer 26 is made of a hydrogel or an ethylcellulose gel. Water is irreversibly bound in these gels.

The mode of operation of the sensor is based on the fact that a gas to be determined, for example carbon dioxide, is absorbed by polymer layer 26. The gas dissolves in the bound water of polymer layer 26 and changes the pH value of the latter. Since a pH sensitive electrode is used as measuring electrode 14, the change of the pH value results in a change of the potential at measuring electrode 14. The change in potential can be measured as a changing voltage between measuring electrode 14 and reference electrode 16. Measuring electrode 14 can take on any specific embodiment that is suited for detecting a change in the pH value of the surroundings with sufficient precision. Especially suited are conductive metal oxide pH electrodes that have for example a surface layer of mixed iridium oxides ($IrO_2$) or ruthenium oxides ($RuO_x$). However, platinum and rhodium electrodes are suitable as well.

FIG. 3 shows another possible specific embodiment of the sensor according to the present invention. The moisture content can be determined by measuring the conductivity of the polymer film. Since the signal for the $CO_2$ concentration is a function of the moisture content, by also taking the moisture content into consideration, this system is able to determine the $CO_2$ content more exactly, i.e. without the influence of moisture. The construction shown in FIG. 3 is used for this purpose.

At a high-impedance resistor 28, the voltage drop U produced by the potential difference of the sensor is measured. Alternatively, by switching the two switches 30, 32, it is possible to determine the conductivity or the resistance of the sensor element by applying a voltage (DC or AC voltage) and by measuring the current flowing through. By arranging two evaluation units at one pair of electrodes 14, 16, it is consequently possible to compensate the moisture-dependency of the sensor signal.

In order to be able to absorb acidic gases—that is, gases such as carbon dioxide, nitrogen oxides or sulfur oxides which in contact with water result in an acidic solution—as quickly as possible and in sufficient quantity in polymer layer 26, the latter preferably contains a strong base such as tetraalkyl ammonium hydroxides or tetraalkyl ammonium hydrogen carbonates. These increase the solubility of the acidic gases in water that is bound in polymer layer 26 by removing the acid produced in the dissolving process.

For determining gases that react in a basic manner such as ammonia, an acid such as a sulphonic acid, for example, is preferably added to polymer layer 26. This promotes the solubility of basic gases in polymer layer 26. Moreover, polymer layer 26 may contain homogenization agents such as tensides for example.

For manufacturing sensor 10, an electrode paste preferably containing ceramic and metallic components, a so-called cermet, is applied onto substrate 12 and is sintered with the ceramic substrate 12. Polymer layer 26 is applied onto the electrode set-up in that a solution containing the polymer, a base or acid and other additives is deposited or imprinted and the solvent is removed. The polymer layer has a layer thickness of 10 to 100 μm, preferably between 20 and 40 μm.

Electrodes 14, 16 are contacted via circuit traces 22, 24, which are either formed also as cermet in one step together with electrodes 14, 16 or by imprinting a solution containing a hardenable resin and a precious-metal component and subsequent hardening of the solution. The use of a silver-containing epoxy resin is preferred.

The present invention is not limited to the exemplary embodiment described, but other specific embodiments in addition to the sensor described are conceivable as well.

Thus, for example, an activated carbon layer can be provided on polymer layer 26 to prevent the entry of gases that damage polymer layer 26 such as nitrogen oxides or sulfur oxides. Furthermore, a temperature measuring unit may be additionally provided for compensating temperature influences on the measured potential differences.

What is claimed is:

1. A sensor for determining a concentration of a gas in a gas mixture, comprising:
   a measuring electrode;
   a reference electrode;
   a polymer layer in contact with the gas mixture and the measuring electrode; and
   at least one evaluation unit for measuring a conductivity of the polymer layer;
   wherein the polymer layer includes a base configured to increase solubility of acidic gases in the polymer layer;
   wherein the polymer layer contains a quaternary ammonium compound as the base including one of tetraalkyl ammonium hydroxides and tetraalkyl ammonium hydrogen carbonates.

* * * * *